(12) United States Patent
Tang (10) Patent No.: US 10,842,820 B2
(45) Date of Patent: Nov. 24, 2020

(54) KITS AND METHODS FOR PROCESSING STEM CELLS FROM BONE MARROW OR UMBILICAL CORD BLOOD

(71) Applicant: Mingqi Tang, Beijing (CN)

(72) Inventor: Mingqi Tang, Beijing (CN)

(73) Assignee: Mingqi TANG, Beijing (CN)

( * ) Notice: Subject to any disclaimer, the term of this patent is extended or adjusted under 35 U.S.C. 154(b) by 135 days.

(21) Appl. No.: 14/971,993

(22) Filed: Dec. 16, 2015

(65) Prior Publication Data

US 2016/0101134 A1  Apr. 14, 2016

Related U.S. Application Data

(62) Division of application No. 14/203,152, filed on Mar. 10, 2014, now Pat. No. 9,241,959.

(60) Provisional application No. 61/780,506, filed on Mar. 13, 2013.

(51) Int. Cl.
| | | |
|---|---|---|
| *A61K 35/28* | (2015.01) | |
| *A61K 35/51* | (2015.01) | |
| *C12N 5/0789* | (2010.01) | |
| *C12N 5/0775* | (2010.01) | |
| *A61K 35/12* | (2015.01) | |

(52) U.S. Cl.
CPC .............. *A61K 35/28* (2013.01); *A61K 35/51* (2013.01); *C12N 5/0647* (2013.01); *C12N 5/0663* (2013.01); *C12N 5/0665* (2013.01); *A61K 2035/124* (2013.01)

(58) Field of Classification Search
CPC .. A61K 35/28; A61K 35/51; A61K 2035/124; C12N 5/0647; C12N 5/1663; C12N 5/0665
See application file for complete search history.

(56) References Cited

U.S. PATENT DOCUMENTS

2006/0210544 A1 * 9/2006 Honmou ................ A61K 35/28
424/93.21
2011/0070202 A1 * 3/2011 Yarowsky ............ A61K 9/0009
424/93.7

FOREIGN PATENT DOCUMENTS

| | | | |
|---|---|---|---|
| CN | 1793340 | A | 6/2006 |
| CN | 1920012 | A | 2/2007 |
| CN | 1948467 | A | 4/2007 |
| CN | 101089176 | A | 12/2007 |
| CN | 101144070 | A | 3/2008 |
| CN | 101638637 | A | 2/2010 |
| CN | 102154201 | A * | 8/2011 |
| WO | WO-2010007620 | A1 * | 1/2010 ............. A61K 35/30 |

OTHER PUBLICATIONS

Hathaway et al., "The Acridine Orange Viability Test Applied to Bone Marrow Cells I. Correlation with Trypan Blue and Eosin Dye Exclusion and Tissue Culture Transformation", Blood, vol. 23, No. 4, Apr. 1964, pp. 517-525.
Lecoeur, Nerve, "Nuclear Apoptosis Detection by Flow Cytometry: Influence of Endogenous Endonucleases", Experimental Cell Research, vol. 277, No. 1, Jul. 1, 2002, pp. 1-14.
Restriction Requirement received for U.S. Appl. No. 14/203,152, dated May 27, 2015, 7 pages.
Notice of Allowance received for U.S. Appl. No. 14/203,152, dated Oct. 6, 2015, 13 pages.

* cited by examiner

*Primary Examiner* — Teresa E Knight
(74) *Attorney, Agent, or Firm* — Morrison & Foerster LLP (57) ABSTRACT

Provided herein are kits for processing stem cells from bone marrow or umbilical cord blood, comprising: a) a precipitation reagent comprising an aqueous solution of 0.1-30% hydroxyethyl starch or 0.1-30% methyl cellulose, and 0.1-20% of cerebroprotein hydrolysate; and b) a separation reagent comprising an aqueous solution comprising Ficoll and diatrizoate and having a density of 1.0-1.2 g/ml, and methods of use. Further provided herein is a collection of stem cells obtained by the kits and methods disclosed herein comprising stem cells from bone marrow or umbilical cord blood, and uses thereof.

4 Claims, 1 Drawing Sheet

KITS AND METHODS FOR PROCESSING STEM CELLS FROM BONE MARROW OR UMBILICAL CORD BLOOD

CROSS REFERENCE TO RELATED APPLICATIONS

This application is a divisional application of U.S. application Ser. No. 14/203,152, filed Mar. 10, 2014, which claims the priority benefit of U.S. provisional application Ser. No. 61/780,506, filed Mar. 13, 2013, the contents of which applications are incorporated herein by reference in their entireties.

TECHNICAL FIELD

The present invention is in the field of biotechnology, and relates to the area of stem cell isolation. Specifically, the present invention relates to stem cell isolation from bone marrow or umbilical cord blood.

BACKGROUND ART

Methods commonly used for the separation of human blood cells include immunomagnetic beads, flow cytometry, blood cell separator and culture amplification. The immunomagnetic beads are coated with known antibodies, and then mixed with human blood. Antigen-positive cells adhere to the immunomagnetic beads, which are passed through a magnetic pipe. The magnetic beads are adsorbed on the wall of the magnetic pipe. After the cells not bound to the magnetic beads pass through, the magnetism of the pipe is removed, and cells bound to the magnetic beads are collected. This method is associated with relatively higher cost, and may not be available to low- and middle-income patients. It may also affect the activity of cells and the effectiveness of cell therapy.

The cell sorting function of methods using flow cytometry is accomplished by the cell sorter. The process consists of the following steps: a liquid column emitted from a nozzle is divided into a series of small water droplets; each is determined whether it will be sorted according to a parameter selected by the logic circuit; then the selected cell droplet is charged by a charging circuit; charged droplets carrying cells deflect when passing through an electrostatic field, and fall into the collector; the rest of the liquid is sucked out as waste. Certain types of instrument use a capture tube for sorting. There are cost and safety concerns for clinical uses of this method.

The method using blood cell separator is mainly used to separate peripheral blood cells. Patients are given a mobilization agent, then the patients' peripheral blood is cycled and filtered by a cell separator. Cells with a diameter within a certain range are collected for cell therapy. The mobilization agents used in this method, however, may increase treatment burden. The volume of separated fluid containing cells may also be too large for clinical use, and patients may bear certain life-threatening risks.

Culture amplification involves collecting human blood, adding reagents to the blood sample and culturing the sample in incubator. The cells are washed before use after about one week in culture. The prolonged time of tissue culture is often accompanied by high risks of contamination, in addition to unknown direction of stem cell differentiation.

Existing technologies of bone marrow and blood separation include those disclosed in Chinese Patent Application No. 200510130326.7, entitled "A method of separating cells and specialized cell separation medium." Various adjustments are required to adapt the method for chicken, bovine, and human blood. There is also plenty of room for improving the accuracy of separating the desired cells. The use of surfactants and the unknown identity of isolated cells are additional concerns for applying this method in the clinic. Thus, the method so far has only been used for simple tests.

Another stem cell separation medium and method is disclosed in Chinese Patent Application No. 200610035900.5, entitled "A stem cell separation medium and its use for stem cell isolation." To practice this method, it is necessary to prepare working solutions, and to adjust the density of cell suspensions because cells can only be collected within the density range of 1.083 g/ml. This method collects a heterogeneous population of cells, which may include few desired target cells for therapeutic purposes. For umbilical cord blood, this method may not effectively remove red blood cells, resulting in transplant rejection in patients.

Chinese Patent Application No. 200610114475.9, entitled "Kit for separation of bone marrow mononuclear cells" discloses yet another method. When used to directly isolate stem cells from blood, the kit does not generate enough cells for clinical use. Therefore, this method involves cell culture and risks high rate of contamination. Moreover, cell culture in vitro may not fully recapitulate cellular environment and cell expansion in vivo. Cells so produced may possess the stem cell or progenitor cell morphology but may not have the desired function for use in the clinic.

Chinese Patent Application No. 200610106875.5 discloses kits for in vivo separation of nucleated cells and their use. This kit uses HISTOPAGUE1077, a lymphocyte separation medium with a density of 1.077 g/ml. Most of the cells so separated are lymphocytes, and may contain only a minority of stem cells for therapeutic use. Clinical efficacy of this method is therefore diminished.

Chinese Patent Application No. 200710137781.9 discloses kits for bone marrow and umbilical cord blood stem cell isolation in vivo and uses of such kits. The kit contains lineage cocktail (Lin antibodies), resulting in increased cost and economic burden to low- and middle-income patients and their inability to afford cell therapy. In addition, Lin antibodies may result in a greater burden to wash isolated cells, and consequences of introducing Lin antibodies into the human body remain unknown.

The following methods for isolating stem cells have been used in clinic.

1. Sieving. For example, blood is directly passed through a blood cell separator which acts as a sieve to sort cells by size, and larger cells are selected for use in treatment. The selected cells include populations of erythrocytes, stem cells, leukocytes, lymphocytes, etc., and the resultant volume of cell suspension is approximately 50 ml-150 ml. It is not advisable to directly inject such a large volume of heterogeneous population of cells into the human body for treatment.

2. Labeling. The desired cells are labeled with antibodies for isolation. The labels are then washed off from isolated cells. The carcinogenicity of unknown labels remains to be determined.

3. Negative selection. Unwanted cells in the blood sample are labeled. This method does not require washing the label off the labeled cells, and therefore maintains the original activity of desired cells. Therefore, this method has its advantages and may achieve therapeutic effects. It is well known that cell populations in the blood are kept at equilibrium by complex mechanisms including negative feedback signaling. By negative selection, cells that are not desired for therapeutic use are removed, resulting in disturbances of cell population equilibrium and water/electrolyte imbalance. Additionally, cells are squeezed, diluted and washed in various solutions during centrifugation and separation, which may reduce cell activity and function. Therefore, it remains unknown whether stem cells so isolated are in the best conditions for use in treatment. Likely the cell number and survival rate are reduced, resulting in lower treatment efficacy, need of larger starting blood volume and increased pain in patients.

To improve existing methods for clinical use, the following aspects should be considered:

1. High treatment cost. Equipment used for cell separation (for example, blood cell separator and flow cytometer) is expensive, leading to high cost of treatment, and is not conducive to the promotion and popularization of the treatment options.

2. Low cell activity. Immunomagnetic beads and flow cytometry generate labeled cells. These sorting methods can only accommodate a narrow range of cells to be screened. Labeled cells may exhibit declined activity and viability. Moreover, the metabolism of the labels and consequences of such labels remaining in the human body are unknown.

3. Bulky cell suspension. Cell separator is often used to separate peripheral blood, and subjects are injected with mobilizing agents for 2-7 days before blood collection to mobilize stem cells from the bone marrow into the peripheral blood. The resultant cell suspension from a blood cell separator often exceeds 50 ml in volume, with considerable numbers of remaining erythrocytes. Such bulky, low quality cell suspension may only be used for autologous subcutaneous injection.

4. Long procedure for cell isolation. Cells are cultured for a week before use in the clinic. Such prolonged procedure may miss the best timing for treatment, compromise treatment effect, and risk high rate of contamination in culture.

5. Many traditional separation methods are complex and tedious, and demand high levels of training of professionals performing the tasks. There is a need for improvements in areas ranging from experimental methods to clinical applications. It may be difficult to scale up the traditional methods for large scale production. Traditional methods may also be associated with high experimental costs, high risks of contamination during operation, difficulty in storage and transportation of cell suspensions, limited quantity of isolated cell suspension, and inability to meet the high clinical demand.

Chinese Patent Application No. 200910187212.4, entitled "Human bone marrow, umbilical cord blood, peripheral blood cell processing kit and cell processing method," discloses using 0.9% NaCl solution or PBS as a diluent, using 6% hydroxyethyl starch or 0.2-1% methyl cellulose as a precipitating reagent, and using a solution (density 1.075 g/ml) formulated with Ficoll and meglumine diatrizoate as a separation reagent. This application discloses a method for safe, effective and efficient separation of stem cells suitable for clinical use.

SUMMARY OF THE INVENTION

In a first aspect, provided herein is a kit for processing stem cells from bone marrow or umbilical cord blood, comprising: a) a precipitation reagent comprising an aqueous solution of 0.1-30% hydroxyethyl starch or 0.1-30% methyl cellulose, and 0.1-20% of cerebroprotein hydrolysate; and b) a separation reagent comprising an aqueous solution comprising Ficoll and diatrizoate and having a density of a 1.0-1.2 g/ml.

In some embodiments, the precipitation reagent may comprise 0.3-15% of cerebroprotein hydrolysate. In some embodiments, the precipitation reagent may comprise 0.8-6% of cerebroprotein hydrolysate. In some embodiments, the precipitation reagent may comprise about 1.5-4.5% of cerebroprotein hydrolysate. In some embodiments, the precipitation reagent may comprise about 3% of cerebroprotein hydrolysate.

In some embodiments, the precipitation reagent may comprise 0.5-18% aqueous solution of hydroxyethyl starch or 0.2-8% aqueous solution of methyl cellulose. In some embodiments, the precipitation reagent may comprise about 1.5-12% aqueous solution of hydroxyethyl starch or about 0.3-5% aqueous solution of methyl cellulose. In some embodiments, the precipitation reagent may comprise about 6% aqueous solution of hydroxyethyl starch or about 0.5% aqueous solution of methyl cellulose.

In some embodiments, the separation reagent may comprise an aqueous solution comprising Ficoll and diatrizoate and having a density of about 1.01-1.088 g/ml. In some embodiments, the separation reagent may comprise an aqueous solution comprising Ficoll and diatrizoate and having a density of about 1.035-1.08 g/ml. In some embodiments, the separation reagent may comprise an aqueous solution comprising Ficoll and diatrizoate and having a density of about 1.075 g/ml.

In some embodiments, the precipitation reagent may comprise 0.5-18% aqueous solution of hydroxyethyl starch or 0.2-8% aqueous solution of methyl cellulose, and 0.8-6% of cerebroprotein hydrolysate, and wherein the separation reagent may comprise an aqueous solution comprising Ficoll and diatrizoate and having a density of about 1.01-1.088 g/ml. In some embodiments, the precipitation reagent may comprise about 1.5-12% aqueous solution of hydroxyethyl starch or about 0.3-5% aqueous solution of methyl cellulose, and about 1.5-4.5% of cerebroprotein hydrolysate, and wherein the separation reagent may comprise an aqueous solution comprising Ficoll and diatrizoate and having a density of about 1.035-1.08 g/ml. In some embodiments, the precipitation reagent may comprise about 6% aqueous solution of hydroxyethyl starch or about 0.5% aqueous solution of methyl cellulose, and about 3% of cerebroprotein hydrolysate, and wherein the separation reagent may comprise anaqueous solution comprising Ficoll and diatrizoate and having a density of about 1.075 g/ml.

In some embodiments, the aqueous solution may use sterile water suitable for injection into a subject, wherein the subject may be a human being. In some embodiments, the precipitation reagent and the separation reagent may be sterilized under ultrafiltration conditions.

In a second aspect, provided herein is a method for separating stem cells using a kit for processing stem cells from bone marrow or umbilical cord blood comprising a precipitation reagent comprising an aqueous solution of 0.1-30% hydroxyethyl starch or 0.1-30% methyl cellulose, and 0.1-20% of cerebroprotein hydrolysate; and a separation reagent comprising an aqueous solution comprising Ficoll and diatrizoate and having a density of 1.0-1.2 g/ml, which method comprises: a) providing a bone marrow or umbilical cord blood sample; b) adding the precipitation reagent to the bone marrow or umbilical cord blood sample, mixing and letting the solution to settle, followed by centrifugation of the top solution to obtain a concentrated sample; and c) adding the concentrated sample from step b) on top of the separation reagent to obtain a collection of cells, wherein the collection of cells comprises stem cells.

In some embodiments, step a) may further comprise adding an anticoagulant to the bone marrow or umbilical cord blood sample. In some embodiments, step a) may further comprise adding an equal volume of saline (NaCl injection) to the bone marrow or umbilical cord blood sample to obtain a diluted sample. In some embodiments, step c) may further comprise adding the concentrated sample from step b) on top of the separation reagent followed by centrifugation. In some embodiments, step a) may be performed in a sterile environment. In some embodiments, the collection of cells may form a cloudy or oily layer after centrifugation.

In some embodiments, the bone marrow may be obtained by a bone marrow needle using a posterior superior iliac spine method with local anesthesia. In some embodiments, the ratio between the diluted sample and the precipitation reagent may be 2:1 by volume. In some embodiments, the concentrated sample from step b) may be diluted with saline.

In some embodiments, the bone marrow or umbilical cord blood sample may be freshly collected from a mammal, wherein the mammal may be a human being. In some embodiments, the bone marrow or umbilical cord blood sample may not have been cultivated ex vivo.

In a third aspect, provided herein is a collection of stem cells obtained by the method disclosed herein comprising stem cells from bone marrow or umbilical cord blood.

In some embodiments, the recovery rate of the stem cells may be at least 80%, at least 85%, or at least 90%. In some embodiments, the survival rate of the stem cells may be at least 90%, at least 95%, or at least 98%. In some embodiments, the stem cells may comprise hematopoietic stem cells (HSC). In some embodiments, the stem cells may comprise mesenchymal stem cells (MSC).

In a fourth aspect, provided herein is a method of treating a disease condition in a subject comprising administrating a collection of stem cells disclosed herein to said subject.

In some embodiments, the disease condition may be selected from the group consisting of Parkinson's, Alzheimer's, cerebral complications, diabetes, diabetic foot, pediatric cerebral palsy, cirrhosis, and systemic lupus erythematosus. In some embodiments, the method may comprise injecting the collection of cells into the vein of the subject. In some embodiments, the method may comprise injecting the collection of cells into the lesion site of the subject through the femoral artery, such as the liver aorta.

In some embodiments, a collection of pluripotent stem cells may be used. In some embodiments, at least $10^6$, at least $10^7$ or at least $10^8$ stem cells may be used. In some embodiments, at least $10^7$-$10^8$ stem cells may be used. In some embodiments, the collection of stem cells may be from the subject being treated, or one or more other subjects.

In some embodiments, stem cells isolated using methods and kits described herein may comprise at least 1%, 1.1%, 1.2%, 1.3%, 1.4%, 1.5%, 2%, 3% or more of CD34$^+$ cells.

DETAILED DESCRIPTION OF THE INVENTION

In order to overcome disadvantages using the technologies in the prior art, such as low recovery rate of target stem cells, large number of untapped stem cells in the waste liquid, and low survival rate of the isolated stem cells, the present invention provides a kit for processing stem cells from human bone marrow or umbilical cord blood. The present invention increases the recovery rate and survival rate of the stem cells isolated from the human bone marrow or umbilical cord blood.

The present invention provides kits for processing stem cells from bone marrow or umbilical cord blood, and methods for isolating stem cells using the kits. One embodiment of the invention comprises a precipitation solution and a separation solution. The first solution comprises a cerebroprotein hydrolysate, and effectively improves the activity and the number of stem cells of the treated samples. Using the present invention for stem cell processing, the recovery rate of target stem cells is increased by about 20% to 30%. The present invention can effectively reduce the amount of human bone marrow or umbilical cord blood sample needed for stem cell isolation. The present invention maintains a high cell survival rate, while greatly improves numbers and activity of isolated stem cells, resulting in their efficient use.

In summary, the present invention has the following features:

1. The cerebroprotein hydrolysate of the present invention increases stem cell numbers recovered.
2. The present invention retains stem cell activity. Stem cell suspension so generated is small in volume and takes only a short time to obtain (about 1 hour).
3. The present invention is particularly suitable for the separation of cells from human bone marrow or umbilical cord blood.
4. The present invention is safe to practice, and endotoxin content of the stem cell suspension is low and in line with the requirements of clinical use. In addition, the procedure does not cause pollution to the environment or contamination of stem cells.
5. Materials for practicing the present invention are easy to obtain at low costs. The procedure is easy to follow and the kits are easy to store and transport. In some aspects, methods of the present invention are automated, and kits are produced by large scale production. Therefore, the present invention provides a much needed method of separating stem cells from bone marrow or umbilical cord blood in the clinic.

A. DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. In another example, a description of a range in weeks also includes disclosure of the days between the week endpoints. This applies regardless of the breadth of the range.

All publications, including patent documents and scientific articles, referred to in this application and the bibliography and attachments are incorporated by reference in their entireties for all purposes to the same extent as if each individual publication were individually incorporated by reference.

The term "umbilical cord blood" is used herein to refer to blood obtained from a neonate or fetus, most preferably a neonate and preferably refers to blood that is obtained from the umbilical cord or the placenta of newborns. Preferably, the umbilical cord blood is isolated from a human newborn. The use of umbilical cord blood as a source of stem cells is advantageous because it can be obtained relatively easily and without trauma to the donor. Umbilical cord blood cells can be used for autologous transplantation or allogenic transplantation, when and if needed. Umbilical cord blood is preferably obtained by direct drainage from the cord and/or by needle aspiration from the delivered placenta at the root and at distended veins.

As used herein, a "stem cell" is a cell from the embryo, fetus, or adult that has, under appropriate conditions, the ability to be cultured for through several divisions without differentiating or dying. Further, a stem cell can, under appropriate conditions, differentiate into at least two distinct cell types.

As used herein, a "pluripotent stem cell" has the ability to differentiate into at least two cell types belong to different germ layer lineages (mesoderm, endoderm, and ectoderm) from which all the cells of the body arise. Pluripotent cells may be obtained from embryos.

An "adult stem cell" is a stem cell isolated from adult (i.e., non-embryo tissue). Adult stem cells as all stem cells are capable of making identical copies of themselves through numerous rounds of culture. This property is referred to as "self-renewal." Adult stem cells typically generate progenitor or precursor cells under appropriate conditions, which then further differentiate or develop into mature cell types that have characteristic shapes and specialized functions, e.g., cells that form blood vessel walls. Adult stem cells can be isolated from numerous tissues including, by way of example, brain, bone marrow, periosteum, blood vessels, skeletal muscle, epithelia of the skin and digestive system, cornea, dental pulp of the tooth, retina, liver, pancreas, and adipose tissue.

The term "administration" or "administering" is used throughout the specification to describe the process by which cells of the subject invention, such as stem cells obtained from umbilical cord blood, or more differentiated cells obtained therefrom, are delivered to a patient for therapeutic purposes. Cells of the subject invention be administered a number of ways including, but not limited to, parenteral (such term referring to intravenous and intra-arterial as well as other appropriate parenteral routes), intrathecal, intraventricular, intraparenchymal (including into the spinal cord, brainstem or motor cortex), intracisternal, intracranial, intrastriatal, and intranigral, among others which term allows cells of the subject invention to migrate to the ultimate target site where needed. The compositions according to the present invention may be used without treatment with a mobilization agent or differentiation agent ("untreated" i.e., without further treatment in order to promote differentiation of stem cells obtained from the umbilical cord blood sample) or after treatment ("treated") with a differentiation agent or other agent which causes certain stem and/or progenitor cells to differentiate into cells exhibiting a differentiated phenotype, such as a neuronal and/or glial phenotype.

Administration will often depend upon the disease or condition treated and may preferably be via a parenteral route, for example, intravenously, by administration into the cerebral spinal fluid or by direct administration into the affected tissue in the brain. For example, in the case of Alzheimer's disease, and Parkinson's disease, the route of administration may be intravenous administration. In the case of multiple sclerosis, the route of administration may be through the cerebrospinal fluid, or through the femoral artery. In the case of stroke, the route of administration may depend upon where the stroke is, but may be directly into the affected tissue (which may be readily determined using MRI or other imaging techniques), or may be administered systemically. In some embodiments of the present invention, the route of administration for treating an individual post-stroke is systemic, via intravenous or intra-arterial administration.

The terms "grafting" and "transplanting" and "graft" and "transplantation" are used synonymously to describe the process by which cells of the subject invention are delivered to the site where the cells are intended to exhibit a favorable effect, such as reconstructing functional insulin-producing beta cells in the pancreas of a diabetes patient, repairing damage to a patient's central nervous system (which can reduce a cognitive or behavioral deficit caused by the damage), treating a neurodegenerative disease or treating the effects of nerve damage caused by stroke, cardiovascular disease, a heart attack or physical injury or trauma or genetic damage or environmental insult to the brain and/or spinal cord, caused by, for example, an accident or other activity. Cells of the subject invention can also be delivered in a remote area of the body by any mode of administration as described above, relying on cellular migration to the appropriate area to effect transplantation. In some embodiments, the cells are co-administered with a blood brain barrier permeabilizer.

Throughout the disclosure, the aqueous solution comprising Ficoll and diatrizoate is described in density. For example, the density of the aqueous solution comprising Ficoll and diatrizoate may be about 1.0-1.2 g/ml, about 1.01-1.088 g/ml, about 1.035-1.08 g/ml, or about 1.075 g/ml.

B. KITS FOR ISOLATING STEM CELLS AND METHODS OF USE

The present application improves upon the stem cell isolation kit by including an appropriate amount of cerebroprotein hydrolysate in the precipitation reagent. By doing so, the recovery rate and survival rate of stem cells are both improved, leading to more usefulness of the isolated stem cells in therapeutic, cosmetic and nutritional applications.

In one aspect, provided herein is a kit for processing stem cells from bone marrow or umbilical cord blood. The kit typically includes two reagents: a) a precipitation reagent comprising an aqueous solution of 0.1-30% hydroxyethyl starch or 0.1-30% methyl cellulose, and 0.1-20% of cerebroprotein hydrolysate; and b) a separation reagent comprising an aqueous solution comprising Ficoll and diatrizoate and having a density of 1.0-1.2 g/ml.

The cerebroprotein hydrolysate added during the separation process contains a large number of amino acids and peptides. Therefore, cerebroprotein hydrolysate restores equilibrium after the removal of cells in the blood and timely provides stem cells with necessary nutrients, thereby promoting stem cell propagation and protein synthesis and improving stem cell energy metabolism. Cerebroprotein hydrolysate can be a sterile reagent isolated from porcine brain tissue after enzymatic hydrolysis.

In addition, cerebroprotein hydrolysate also degrades fibrous protein particles produced in the isolation process, thereby avoiding formation of thrombosis in stem cell therapy. Cerebroprotein hydrolysate also prevents the deterioration of stem cell quality due to manipulation of cells and other external stimuli in the isolation process. The inventor has observed the formation of fibrous protein particles visible to the naked eye during stem cell separation, due to centrifugal effects and low temperature conditions. If the stem cell suspension used for treatment contains such fibrous protein particles, smaller vessels in the body will be blocked so that stem cells cannot efficiently reach the target tissue for cellular repair. Visible fibrous protein particles no longer form when cerebroprotein hydrolysate is added, leading to safer and more effective clinical treatment.

Any suitable sources of cerebroprotein hydrolysate for therapeutic, nutritional or cosmetic purposes may be used in the present invention. For example, the cerebroprotein hydrolysate can be selected from the following products: Chinese Drug Approval Codes H20052182, H20003384, H20003386, or H20003385. Other sources of cerebroprotein hydrolysate include: Cerebroprotein Hydrolysate for Injection (Hainan Universal Alliance Pharmaceutical Co., Ltd.); Cerebroprotein Hydrolysate for Injection (Cognistar, Shenzhen Mellow Hope Pharm Industrial Co., Ltd., Shenzhen, China); Cerebroprotein Hydrolysate for Injection (Mercatorpharma, Shanghai, China), etc.

The percentage of cerebroprotein hydrolysate in the precipitation reagent of the kit may vary in order to optimize the recovery rate and/or survival rate of the stem cells isolated using the kit. As used herein, the percentage of the aqueous solutions of any of the components is calculated by weight. For example, in some embodiments, the precipitation reagent may comprise 0.3-15% of cerebroprotein hydrolysate. In some embodiments, the precipitation reagent may comprise 0.8-6% of cerebroprotein hydrolysate. In some embodiments, the precipitation reagent may comprise about 1.5-4.5% of cerebroprotein hydrolysate. In some embodiments, the precipitation reagent may comprise about 3% of cerebroprotein hydrolysate.

Similarly, the percentage of Ficoll and diatrizoate in the separation reagent of the kit may vary in order to optimize the recovery rate and/or survival rate of the stem cells isolated using the kit. For example, in some embodiments, the separation reagent may comprise an aqueous solution comprising Ficoll and diatrizoate and having a density of about 1.01-1.088 g/ml. In some embodiments, the separation reagent may comprise an aqueous solution comprising Ficoll and diatrizoate and having a density of about 1.035-1.08 g/ml. In some embodiments, the separation reagent may comprise an aqueous solution comprising Ficoll and diatrizoate and having a density of about 1.075 g/ml. Sodium diatrizoate, meglumine diatrizoate, or a combination thereof at various ratios may be used for the separation reagent.

The kits described herein may further comprise reagents, which include, but are not limited to, substrates, labels, negative or positive controls for hybridization and detection, tubes and/or other accessories, reagents for collecting tissue sample, buffers, hybridization chambers, cover slips, etc., and may also contain a software package, e.g., for analyzing recovery rate and/or survival rate of stem cells using statistical methods as described herein, and optionally a password and/or account number for assessing the compiled database.

Figure 1:
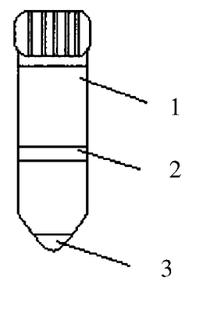
FIG. 1 shows a schematic distribution of cell populations after separation of a blood sample. 1: serum layer; 2: nucleated cell and stem cell layer; 3: red blood cell layer.

Further provided herein are methods for separating stem cells using the kits disclosed herein from bone marrow or umbilical cord blood, which comprise: a) providing a bone marrow or umbilical cord blood sample; b) adding the precipitation reagent to the bone marrow or umbilical cord blood sample, mixing and letting the solution to settle, followed by centrifugation of the top solution to obtain a concentrated sample; and c) adding the concentrated sample from step b) on top of the separation reagent to obtain a collection of cells, wherein the collection of cells comprises stem cells. In some embodiments, the collection of stem cells may form a cloudy or oily layer after centrifugation, shown as layer 2 in FIG. 1.

Any suitable method may be used for bone marrow collection. In some embodiments, bone marrow collection may include: extracting 1-1.5 ml sodium citrate solution into a bone marrow needle; using a posterior superior iliac spine method with local anesthesia to collect bone marrow with the bone marrow needle to a total volume of 5 ml. Following the bone marrow collection, the bone marrow may be injected into a sterile bottle as pretreatment samples of bone marrow.

Any suitable method may be used for umbilical cord blood collection. In some embodiments, umbilical cord blood collection my include: after falling off of the placenta, using a single blood collection bag containing sodium citrate solution, inserting the needle of the blood collection bag into the umbilical vein, collecting blood while gently shaking the blood bag in order to mix anticoagulant solution fully with the umbilical cord blood, resulting in a umbilical cord blood pretreatment sample.

In some embodiments, the bone marrow or umbilical cord blood pretreatment sample is diluted with the precipitation solution at a volume ratio of 1:1. In some embodiments, the diluted sample is mixed with the precipitation solution at a volume ratio of 2:1 in step b). The mixture is shaken for 1-8 minutes, let stand for 3 minutes to 3 hours to allow separation of layers, and the upper layer of cell suspension is drawn into a 50 ml centrifuge tube. The cell suspension is centrifuged for 1-20 minutes at 500-4000 rpm. The lower layer of cell suspension is collected to obtain the concentrated sample.

In some embodiments, the concentrated sample from step b) is diluted with saline and placed on top of the separation solution, and centrifuged for 1-60 minutes at 500-4000 rpm. A cloudy or oily stem cell layer of approximately 2-4 mm in thickness in the middle of the centrifuge tube may then be collected.

In some embodiments, the collected stem cell layer is washed with saline 1-5 times and then diluted with physiological saline to volumes suitable for clinical use. In some embodiments, steps a) and b) are carried out under sterile conditions.

C. ISOLATED STEM CELLS AND USES THEREOF

In another aspect, provided herein is a collection of stem cells obtained by the methods disclosed herein comprising stem cells from bone marrow or umbilical cord blood. As discussed above, the kits and methods disclosed herein improve the recovery rate and survival rate of stem cells isolated from bone marrow or umbilical cord blood.

As used herein, recovery rate refers to the percentage of total number of stem cells isolated from a sample, such as a bone marrow sample or an umbilical cord blood sample. For example, in some embodiments, the recovery rate of the stem cells is at least 50%, 60%, 70%, 80%, 85%, 90%, 95%, 98%, 99%, or higher. The number of stem cells may be counted using any suitable device known to a person of ordinary skill in the art, such as a counting chamber, spectrophotometer, flow cytometer, etc. In some embodiments, at least $10^6$, $10^7$, $10^8$, $2\times10^8$, $3\times10^8$, $4\times10^8$, $5\times10^8$, $10^9$, or more stem cells may be isolated from a single sample. In some embodiments, at least $10^7$-$10^8$ stem cells may be isolated from a single sample.

In some embodiments, stem cells are identified and characterized by fluorescence-activated cell sorting (FACS). In some embodiments, the fluorescence-activated cell sorting is performed with monoclonal antibodies to cell markers. In certain embodiments, the cell markers may be CD34, CD90/Thy1, CD59, CD38, CD105 and/or c-Kit. In one embodiment, hematopoietic stem cells are identified and characterized as a $Lin^-CD34^+CD90^+$ progenitor cell population. In another embodiment, the hematopoietic stem cell population is identified and characterized as $Lin^-CD34^+CD59^+CD90^+$ $CD38^{low/-}$c-$Kit^{-/low}$. In some embodiments, stem cells are identified and characterized by cell morphology, including that of the nucleus. In some embodiments, stem cells are characterized by the presence of a large, round nucleus. In some embodiments, stem cells isolated using methods and kits described herein may comprise at least 1%, 1.1%, 1.2%, 1.3%, 1.4%, 1.5%, 2%, 3% or more of $CD34^+$ cells.

As used herein, survival rate refers to the percentage of live stem cells in the total number of stem cells isolated from a sample, such as a bone marrow sample or an umbilical cord blood sample. For example, in some embodiments, the survival rate of the stem cells is at least 50%, 60%, 70%, 80%, 85%, 90%, 95%, 98%, 99%, or higher. The live stem cells and/or dead stem cells may be identified using any suitable method known to a person of ordinary skill in the art, such as eosin dye exclusion (Hathaway et al. (1964) Blood 23 (4): 517-525), propidium iodide staining (Lecoeur H (2002) Exp. Cell Res. 277 (1): 1-14), trypan blue dye exclusion, erythrosine staining, 7-Aminoactinomycin D staining, etc.

Umbilical cord is a source typically used for hematopoetic stem cell (HSC) transplantation. Cord blood HSCs have a naïve state with minimal exposure to the environment (intact genome), high proliferation capacity, and differentiation potential. There are currently identified two major types of stem cells found in bone marrow: HSCs (or $CD34^+$ cells) are capable of differentiating into all types of blood and immune cells, and stromal (mesenchymal) stem cells (MSC) that are typically considered to form bone, cartilage, muscle and fat. In some embodiments, stem cells isolated using methods and kits described herein may comprise at least 1%, 1.1%, 1.2%, 1.3%, 1.4%, 1.5%, 2%, 3% or more of $CD34^+$ cells.

Further provided herein is a method of treating a disease condition in a subject comprising administrating a collection of stem cells disclosed herein to the subject. In some embodiments, the subject may be diagnosed with the disease condition, and the collection stem cells may be used to treat the disease condition. The collection of stem cells may be isolated from the same subject, or from one or more other subjects. In some embodiments, the subject may be a human being.

Because of the improved recovery rate, survival rate, and other characteristics of the stem cells isolated using the kits and methods disclosed herein, the stem cells are suitable to treat a variety of conditions, including disease conditions, cosmetic conditions, nutritional conditions, etc. For example, in some embodiments, the collection of stem cells may be used in the treatment of Parkinson's disease, Alzheimer's disease, cerebral thrombosis and complications, diabetes, diabetic foot, cerebral palsy, liver cirrhosis, systemic lupus erythematosus and other diseases with cellular damage. In some embodiments, at least 300, at least $10^6$, at least $10^7$ or at least $10^8$ or more stem cells may be used for treating a subject.

D. EXAMPLES

The following examples are intended to further describe and illustrate various aspects of the invention, but not to limit, the scope of the invention in any manner, shape, or form, either explicitly or implicitly.

Example 1

Preparation of Stem Cell Processing Kits

The kit for stem cell processing of the present invention was prepared as follows. The density separation of stem cells comprised two steps. The first solution was used to begin the process, and the second solution was used to complete the process.

150 ml of the first solution was prepared using either a 0.1-30% (w/w) aqueous solution of hydroxyethyl starch, or a 0.1 to 30% (w/w) aqueous solution of methyl cellulose. 0.1-20% of cerebroprotein hydrolysate was added.

80 ml of the second solution was prepared as a separation reagent (density 1.0-1.2 g/ml) using Ficoll and meglumine diatrizoate. The second solution was prepared in large volumes, for example, in a 500 ml culture bottle, to eliminate the need of multiple procedures for stem cell isolation thereby reducing the risks of contamination.

The first and second solutions were sterilized under ultrafiltration conditions. Endotoxin levels in the first and second solutions were less than or equal to 0.5 EU/ml.

Table 1 shows exemplary concentrations of components of the first solution and exemplary densities of the second solution. Any combination of the first solution and the second solution, as disclosed herein, may be used.

TABLE 1

Exemplary concentrations of the first solution and densities of the second solution

| The first solution | | | |
|---|---|---|---|
| hydroxyethyl starch concentration (w/w) | methyl cellulose concentration (w/w) | cerebroprotein concentration (w/w) | The second solution Density: g/ml |
| 0.3% | | 0.2% | 1.02 |
| 1.0% | | 0.4% | 1.04 |
| 4.0% | | 0.8% | 1.05 |
| 10% | | 1.0% | 1.065 |
| 15% | | 2.0% | 1.07 |
| 20% | | 3.0% | 1.085 |
| 25% | | 6.0% | 1.09 |
| | 0.3% | 8.0% | 1.095 |
| | 1.0% | 10.0% | 1.10 |
| | 4.0% | 12.0% | 1.12 |

TABLE 1-continued

Exemplary concentrations of the first solution and densities of the second solution

| The first solution | | | |
|---|---|---|---|
| hydroxyethyl starch concentration (w/w) | methyl cellulose concentration (w/w) | cerebroprotein concentration (w/w) | The second solution Density: g/ml |
| | 10% | 14.0% | 1.125 |
| | 15% | 14.0% | 1.145 |
| | 20% | 16.0% | 1.16 |
| | 25% | 18.0% | 1.18 |

Example 2

Use of Kits for Stem Cell Processing (Samples 1-10)

Experimental Group (Group A)

Kits for stem cell processing were used as follows.

(1) In both the experimental and control groups, blood samples were collected from the same voluntary donor's bone marrow blood or umbilical cord blood. After mixing with the anticoagulant solution (sodium citrate), the blood samples were divided into two equal portions of 50 ml or 90 ml each. One portion was added into a sterile culture bottle, and mixed with an equal volume of sodium chloride solution for injection.

(2) The diluted sample was mixed with the first solution at a volume ratio of 2:1. The mixture was shaken for 1-8 minutes, let stand for 3 minutes to 3 hours to allow separation of layers, and the upper layer of cell suspension was drawn into a 50 ml centrifuge tube. The cell suspension was centrifuged for 1-20 minutes at 500-4000 rpm. The lower layer of cell suspension was collected to obtain the concentrated sample.

(3) The concentrated sample from step (2) was diluted with saline and placed on top of the second solution, and centrifuged for 1-60 minutes at 500-4000 rpm. An oily stem cell layer of approximately 2-4 mm in thickness in the middle of the centrifuge tube was then collected. See FIG. 1. This stem cell layer was not disrupted even when being collected with a suction tube. The layer became thinner as stem cells were collected. Collection was continued until all stem cells were collected.

4) The collected stem cells were washed with physiological saline 1-5 times and then diluted with physiological saline to volumes suitable for clinical use. Group A data was collected and recorded.

Control Group (Group B)

Control experiments for stem cell processing were conducted as follows.

The other half of the bone marrow or umbilical cord blood was subjected to the sample experimental procedures and conditions as in Group A, except that the second solution did not contain cerebroprotein hydrolysate. Group B data was collected and recorded.

Data for stem cell processing and control experiments is shown in Tables 2-3, in which Group A presents stem cell processing according to the present invention, and Group B represents control experiments without using cerebroprotein hydrolysate.

The number of stem cells and survival rate in the tables were determined using medical microscope, hemacytometer, and trypan blue staining, in accordance with the method described in Clinical Laboratory Technology, 2011, published by the People's Health Publishing House.

TABLE 2

Processing of umbilical cord blood stem cells as compared to control group

Source: Umbilical cord blood

| No. | Sample Volume (ml) | Group | Total stem cell numbers before isolation ($10^8$) | Total stem cell numbers after isolation ($10^8$) | Recovery (%) | Viability (%) | Group A Recovery higher than Group B by (%) |
|---|---|---|---|---|---|---|---|
| 1 | 50 | A | 2.3 | 2.1 | 91.3 | 99 | 26.1 |
| | | B | | 1.5 | 65.2 | 90 | |
| 2 | 52 | A | 2.5 | 2.2 | 88 | 98 | 28 |
| | | B | | 1.5 | 60 | 88 | |
| 3 | 53 | A | 2.2 | 1.8 | 81.8 | 98 | 31.8 |
| | | B | | 1.1 | 50 | 87 | |
| 4 | 55 | A | 1.8 | 1.6 | 88.9 | 98 | 22.2 |
| | | B | | 1.2 | 66.7 | 90 | |
| 5 | 49 | A | 2 | 1.6 | 80 | 99 | 25 |
| | | B | | 1.1 | 55 | 92 | |

In the above table, 150 ml of the first solution was prepared using a 6% (w/w) aqueous solution of hydroxyethyl starch, or a 0.5% (w/w) aqueous solution of methyl cellulose. 3% of cerebroprotein hydrolysate was added. The cerebroprotein hydrolysate used in this example was the cerebroprotein hydrolysate for injection, manufactured by Hainan Universal Alliance Pharmaceutical Co., Ltd.

80 ml of the second solution was prepared as a separation reagent (density 1.075 g/ml) using Ficoll and meglumine diatrizoate. The second solution was prepared in a 500 ml culture bottle, to eliminate the need of multiple procedures for stem cell isolation thereby reducing the risks of contamination.

The first and second solutions were sterilized under ultrafiltration conditions. Endotoxin levels in the first and second solutions were less than or equal to 0.5 EU/ml.

TABLE 3

Processing of bone marrow stem cells as compared to control group
Source: Bone Marrow

| No. | Sample Volume (ml) | Group | Total stem Cell numbers before isolation ($10^8$) | Total stem cell numbers after isolation ($10^8$) | Recovery (%) | Viability (%) | Group A Recovery higher than Group B by (%) |
|---|---|---|---|---|---|---|---|
| 6 | 80 | A | 4 | 3.6 | 90 | 98 | 20 |
|  |  | B |  | 2.8 | 70 | 90 |  |
| 7 | 85 | A | 3.8 | 3.4 | 89.5 | 98 | 21.1 |
|  |  | B |  | 2.6 | 68.4 | 88 |  |
| 8 | 90 | A | 4.2 | 3.8 | 88.1 | 99 | 19.1 |
|  |  | B |  | 2.9 | 69.1 | 90 |  |
| 9 | 88 | A | 3.7 | 3 | 81.1 | 99 | 21.6 |
|  |  | B |  | 2.2 | 59.5 | 89 |  |
| 10 | 86 | A | 3.5 | 3.1 | 88.6 | 98 | 20 |
|  |  | B |  | 2.4 | 68.6 | 88 |  |

In the above table, 150 ml of the first solution was prepared using a 6% (w/w) aqueous solution of hydroxyethyl starch, or a 0.5% (w/w) aqueous solution of methyl cellulose. 0.9% sodium chloride solution was used. 3% of cerebroprotein hydrolysate was added. The cerebroprotein hydrolysate used in this example was the cerebroprotein hydrolysate for injection, manufactured by Hainan Universal Alliance Pharmaceutical Co., Ltd.

80 ml of the second solution was prepared as a separation reagent (density 1.075 g/ml) using Ficoll and meglumine diatrizoate. The second solution was prepared in a 500 ml culture bottle, to eliminate the need of multiple procedures for stem cell isolation thereby reducing the risks of contamination.

The first and second solutions were sterilized under ultrafiltration conditions. Endotoxin levels in the first and second solutions were less than or equal to 0.5 EU/ml.

Stem cell layers were isolated in Groups A and B, and stem cell numbers and viability were determined.

Group A: stem cell number was 200-300 million, cell viability was 98.5%, and stem cell recovery rate was about 90%.

Group B: stem cell number was 100-200 million, cell viability was 90%, and stem cell recovery rate was about 80%.

The number of stem cells isolated in Group A was more than 10% higher than that in Group B.

Therefore, 50 ml of bone marrow blood is sufficient for stem cell isolation according to the present invention. Bone marrow blood is often collected by drilling in the posterior superior iliac spine, and even with the use of anesthetics, the patient still suffers from a lot of pain. It takes about 50 minutes to collect 100 ml of bone marrow, while it only takes 5-10 minutes to collect 50 ml of bone marrow. The difficulty of bone marrow collection increases as the desired bone marrow amount increases. If only a small amount of bone marrow is needed for isolating enough stem cells for clinical treatment, using the method of the present invention can spare the patients at least 40 minutes of pain.

Example 3

A Systemic Lupus Erythematosus Patient Treated with Stem Cell Therapy

An adult female patient was diagnosed with systemic lupus erythematosus, lupus nephritis (Type IV), and chronic renal insufficiency (stage 5 chronic kidney disease). The patient exhibited facial swelling and severe edema of lower limbs, accompanied by dry mouth, fatigue, dark complexion, and low spirits. Urine lab results were as follows: urine protein 3+, urine occult blood 3+, nitrite 2+, erythrocytes 152.24/HPF, leukocytes 1006.60/HPF, bacteria 17368.36/HPF, 24-hour urine protein quantitation 11.463 g/24 h. Renal function results were: potassium 5.53 mmol/L, urea 25.33 mmol/L, creatinine 446 μmol/L. Complement C3 was 0.25 g/L, complement C4 was 0.09 g/L, and blood IgG was 20.40 g/L. Antinuclear antibody was +1:80, and anti-double stranded DNA was ++. Renal biopsy showed type IV lupus nephritis (active/chronic).

The patient received stem cell therapy, and completed three treatments within about 6 months. Treatments were accompanied by oral corticosteroids Medrol and hydroxychloroquine sulfate treatment for systemic lupus erythematosus. Patient received no other treatment or medication.

Stem cells from the umbilical cord blood of a newborn were used for the treatments. 50-150 ml of umbilical blood was used for processing. Stem cells were separated using a kit consisting of a precipitation reagent that comprises 6% aqueous solution of hydroxyethyl starch and 2% of cerebroprotein hydrolysate, and a separation reagent that comprises an aqueous solution comprising Ficoll and meglumine diatrizoate and having a density of 1.075 g/ml. A total of $2 \times 10^8$ stem cells were obtained. For each treatment, $10^7$-$10^8$ stem cells were administered to the patent.

Patient received the first stem cell therapy by intravenous infusion. No adverse effects were reported the day after receiving treatment. Patient reported no fever, cough or expectoration, chest tightness, shortness of breath, headache or dizziness, or skin rashes. 2-3 days after the treatment, patient reported less fatigue and drowsiness, improved stamina, normal appetite, normal urination and defecation, and sound sleep.

Patient received the second stem cell therapy about one month after the first treatment. Edema of the lower limbs was ameliorated. Patient was in better mental state, the relevant indicators started gradually returning to normal.

The patient received the third stem cell therapy about four month after the second treatment. After the third treatment, systemic edema symptoms disappeared completely, and patient was in good spirit, with no fatigue, no sleepiness, significantly increased physical strength, no fever, no skin and mucous membrane damage, no joint and muscle pain, no thirst, no nausea, no vomiting, normal appetite, normal urination and defecation, and sound sleep.

Various laboratory markers except the urine protein levels returned to almost normal levels or decreased significantly. See Table 4 below. Urine lab results were as follows: urine protein 3+, trace levels of urine occult blood, nitrite–, erythrocytes 6.10/HPF, leukocytes 26.60/HPF, bacteria 902.18/HPF. 24-hour urine protein quantitation was 6.072 g/24 h. Renal function tests were: potassium 4.12 mmol/L, urea 4.91 mmol/L, creatinine 76 μmol/L, and Serum Albumin 25.4 g/L. Other test results were: C3 0.80 g/L, C4 0.24 g/L, immunoglobulin IgG 5.98 g/L, uric acid 302 μmol/L, antinuclear antibody+1:80, and anti-double-stranded DNA antibody–.

TABLE 4

Comparison of patient indicators before and after stem cell therapy

| | Indicators | Before Stem Cell Therapy | After Stem Cell Therapy | Reference Value |
|---|---|---|---|---|
| Kidney Functional Test | Potassium | 5.53H | 4.12 | 3.5-5.2 mmol/L |
| | Sodium | 148.1H | 139.7 | 136.0-145.0 mmol/L |
| | Chloride | 118.2H | 104.3 | 99.0-110.0 mmol/L |
| | Serum bicarbonate | 19.1L | 27.8 | 22.0-29.0 mmol/L |
| | Urea | 21.97H | 4.91 | mmol/L |
| | Creatinine | 446H | 76 | μmol/L |
| Urine Test | Protein | 3+ | 3+ | negative |
| | Urine occult blood | 3+ | trace | negative |
| | Nitrite | 2+ | negative | negative |
| | Erythrocytes | 152.24H | 6.10H | 0.00-3.52/HPF |
| | Leukocytes | 1006.00H | 26.60H | 0.00-3.08/HPF |
| | Epithelial cells | 17.22H | 3.20H | 0.00-1.74/HPF |
| | Bacteria | 17368.30H | 902.18H | 0.00-664.00/HPF |
| Liver Functional Test | Cholinesterase | 4581L | 9732 | 5320-12920 U/L |
| | Prealbumin | 13.80L | 34.80H | 22.00-34.00 mg/dL |
| | Cystatin C | 4.26H | 1.54H | 0.53-0.95 mg/L |
| | γ-glutamyl acylase | 6 L | 22 | 10-47 U/L |
| | Alanine aminotransferase | 4L | 16 | 5-40 U/L |
| | Total protein | 41.6L | 47.1L | 67.0-83.0 g/L |
| | Albumin | 18.8L | 25.4L | 40.0-50.0 g/L |
| | Total bilirubin | 1.0L | 4.7 | 3.4-20.5 μmol/L |
| | Triglycerides | 4.18H | 0.87 | 0.00-1.70 mmol/L |
| | Total cholesterol | 8.26H | 8.20H | 0.00-5.72 mmol/L |
| | High-density lipoprotein cholesterol | 0.68L | 2.01H | 0.91-1.92 mmol/L |
| | Low-density lipoprotein cholesterol | 5.89H | 5.71H | 0.00-3.64 mmol/L |
| Uric acid in blood | Uric acid in blood | 410H | 302 | 155-357 μmol/L |
| Complement | C3 | 0.25L | 0.80 | 0.79-1.52 g/L |
| | C4 | 0.09L | 0.24 | 0.16-0.38 g/L |
| Autoantibodies | Antinuclear antibody. | +1:80 | +1:80 | |
| | Anti-double-stranded DNA antibody | ++ | — | |
| Urine Proteins | 24-hour urinary protein quantification | 12.955H | 6.072H | 0.028-0.141 g/24 h |
| | Urinary protein | 1079.6H | 404.8H | 1.0-14.0 mg/dl |
| | Urine volume per 24-hour | 1200 | 1500 | 1000-1500 ml/24 h |

Example 4

Flow Cytometry for CD34$^+$ Cells in Cells Isolated from Bone Marrow

This example describes identification of CD34$^+$ cells in cells isolated from umbilical cord blood by flow cytometry. Cells were separated from the umbilical cord blood as described above, and 1 mL of the separated cells were counted. The 1 mL separated cells contained 30,278 nucleated cells. Nucleated cells contain mature cells (lymphocytes), and immature cells (stem cells). The 30,278 nucleated cells were stained with FACS antibodies including an anti-CD34 antibody, and subjected to flow cytometry. 403 of the 30,278 nucleated cells were tested positive for CD34, indicating they were positive for the HSC marker.

If the percentage of CD34$^+$ cells in the isolated nucleated cells is <1%, then the ratio of mature cells (lymphocytes) to immature cells (stem cells) does not reach the required threshold. If the percentage of CD34$^+$ cells in the isolated nucleated cells is >1%, then the percentage of immature cells (stem cells) has reached the required threshold of 1%-3%.

In this experiment, the percentage of CD34$^+$ cells in the isolated nucleated cells was 1.33%, which reached the required threshold of 1%-3%, indicating that all the immature cells (stem cells) were isolated.

All headings are for the convenience of the reader and should not be used to limit the meaning of the text that follows the heading, unless so specified.

Citation of the above publications or documents is not intended as an admission that any of the foregoing is pertinent prior art, nor does it constitute any admission as to the contents or date of these publications or documents.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

I claim:

1. A kit for processing stem cells from bone marrow or umbilical cord blood, comprising:
   a) a precipitation reagent which is an aqueous solution consisting of 6% (w/w) hydroxyethyl starch and 3% (w/w) of cerebroprotein hydrolysate; and
   b) a separation reagent which is an aqueous solution comprising diatrizoate and a copolymer of sucrose and epichlorohydrin, wherein the separation reagent has a density of 1.075 g/ml.

2. The kit of claim 1, wherein the aqueous solution contains sterile water suitable for injection into a subject.

3. The kit of claim 2, wherein the subject is a human being.

4. The kit of claim 1, wherein the precipitation reagent and the separation reagent are sterilized under ultrafiltration conditions.

* * * * *